United States Patent
Hartlaub

(10) Patent No.: US 6,348,050 B1
(45) Date of Patent: Feb. 19, 2002

(54) INFUSION SYSTEMS FOR CREATING MICROENVIRONMENTS IN A LIVING BODY

(75) Inventor: Jerome T. Hartlaub, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,033

(22) Filed: Apr. 30, 1999

(51) Int. Cl.⁷ ................................................. A61K 9/22
(52) U.S. Cl. ................................................... 604/891.1
(58) Field of Search ........................... 604/93.01, 891.1, 604/500, 502, 513, 522, 19, 48, 892.1; 128/898

(56) References Cited

U.S. PATENT DOCUMENTS

| | | | |
|---|---|---|---|
| 5,584,885 A | | 12/1996 | Seckel |
| 5,643,207 A | * | 7/1997 | Rise ............................ 604/93 |
| 5,832,932 A | | 11/1998 | Elsberry et al. |
| 5,980,885 A | * | 11/1999 | Weiss et al. ............. 424/93.21 |
| 6,151,525 A | | 11/2000 | Soykan et al. |
| 6,206,914 B1 | | 3/2001 | Soykan et al. |

FOREIGN PATENT DOCUMENTS

| | | |
|---|---|---|
| WO | WO 98/02040 | 1/1998 |
| WO | WO 98/02150 | 1/1998 |

OTHER PUBLICATIONS

Neuronal Regeneration, Reorganization, and Repair, Advances in Neurology, vol. 72, Fredrick J. Seil, M.D., Lippincott–Raven (1977), pp. 113–119 and pp. 121–132.

The Role of Microenvironment in Axonal Regeneration, Advances in Anatomy Embryology and Cell Biology 137, Christine C. Stichel–Gunkel, Springer (1997), pp. 1–81.

CNS Injuries: Cellular Responses and Pharmacological Strategies, Berry et al., CRC Press (1999), pp. 169–189.

Neuroregeneration, Afredo Gorio, Ph.D., Raven Press (1992), pp. 61–62.

Cellular and Molecular Basis of Regeneration, Chapter 17: Regeneration in Brain and Spinal Cord and Chapter 18: Briding the Gap: Restoration of Structure and Function in Humans (undated).

* cited by examiner

Primary Examiner—Anhtuan T. Nguyen
(74) Attorney, Agent, or Firm—Banner & Witcoff, Ltd.

(57) ABSTRACT

The invention provides implantable infusion systems, including apparatus and methods, for prolonged infusion of a carefully designed medicament composition to create and maintain a comprehensive microenvironment at a target area in a living body. The composition may include living cells to treat a particular disease and which deliver exogenous substances to maintain a microenvironment in the living body. The invention contemplates medicament compositions that include stem cells (neuro or otherwise), including homographs and allographs, adhesive peptides, substances which inhibit fiberblast growth, genetically modified cells which produce useful exogenous substances, nerve growth factor (NGF), previously harvested cells from a living body. In another aspect, the invention contemplates the replication of cells in a reservoir, for example, to keep cells alive in a dormant state until infusion.

3 Claims, 3 Drawing Sheets

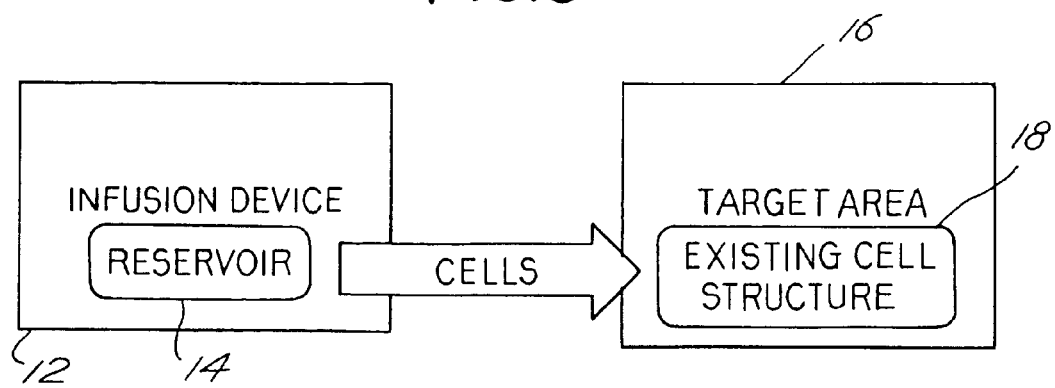
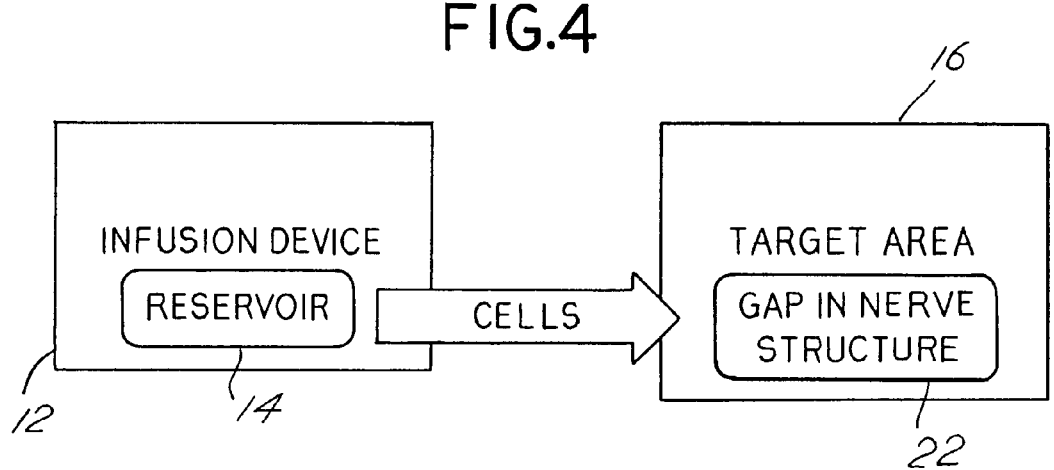

INFUSION SYSTEMS FOR CREATING MICROENVIRONMENTS IN A LIVING BODY

BACKGROUND OF THE INVENTION

1. Field of the Invention

The present invention relates to systems, including methods and apparatus, for delivering therapy to specific sites in a living body. More particularly, the invention relates to implantable infusion systems for creating and maintaining microenvironments in a living body to provide therapeutic effects, including tissue regeneration and production of therapeutic agents for living tissue.

2. Description of Related Art

Microenvironments are spaces, either in vitro or in vivo, wherein specific conditions are controlled and maintained in order to obtain specific therapeutic effects, including, for example, the promotion of tissue regeneration and the introduction or fostering of growth and development of living cells that generate particular therapeutic agents. It is widely recognized that the tissues of the Central Nervous System (CNS) have much less capacity for regeneration than other tissues in the mammalian body. It has been suggested that the some tissues may lack cellular or substrate constituents that are conducive for growth during development (Liesi, 1985, EMBO J. 4:2505-2511; and Carbonetto et al, 1987, J. Neurosci. 7:610-620), or particular sites in the body may contain components which are nonpermissive inhibitory for cell regeneration (Schwab and Thoenen, 1985, J. Neurosci. 5:2415-2423). As a result, recent efforts have focused on the creation and maintenance of microenvironments to aid in the repair of damaged or degenerated area of the CNS. These efforts include, for example, the introduction of cells into the target site, and are described, for example, by Whittemore et al, "Gene Therapy and the Use of Stem Cells for Central Nervous System Regeneration," Advances in Neurology, Vol. 72, pp. 113–119 (1997); Will et al, "Regeneration in Brain and Spinal Cord," Cellular and Molecular Basis of Regeneration From Invertebrates to Humans," pp. 379–397, Wiley & Sons (1998); and Stichel-Gunkel, "The Role of the Microenvironment in Axonal Regeneration," Advances in Anatomy, Embryology and Cell Biology 137, (1997). The entire writings of each of these references are incorporated herein by reference.

It is also known to utilize mechanical implements, such as nerve regeneration chambers, to define and maintain microenvironments in the immediate vicinity of a damaged nerve in the human body to foster the repair and growth of the damaged tissue. For example, U.S. Pat. No. 5,584,885, the entire writing of which is incorporated herein by reference, discloses a nerve regeneration chamber which maintains a microenvironment to promote the regeneration of a damaged nerve. The regeneration chamber includes injection ports and exhaust ports to supply agents to the regeneration chamber and to remove agents from the regeneration chamber. Such techniques require additional implantation and associated trauma in order to place the regeneration chamber at the target site.

It is further known, as exemplified in U.S. Pat. No. 5,832,932 to provide infusion systems for infusing therapeutic agents, in the form of drugs, to specific sites in the human brain to treat movement disorders and other diseases. However, known infusion therapy systems provide only a limited range of non-living substances to treat a target area of the living body and have not heretofore been used to create comprehensive microenvironments in a living body.

What is needed is an infusion system for delivering a carefully designed medicament composition for creating and maintaining a comprehensive microenvironment in a living body. Specifically, what is needed is an implantable infusion system capable of providing a diverse range of medicament compositions, including living and non-living substances, in order to create and maintain a desired microenvironment in a living body for an extended period of time.

SUMMARY OF THE INVENTION

The present invention solves the aforementioned problems by providing a system for infusing a carefully designed medicament composition to achieve a particular desired therapeutic effect. The composition may include living cells to treat a particular disease and which deliver exogenous substances to maintain a microenvironment in the living body. For example, stem cells may be provided in the composition to be introduced into the living body and, in an appropriate environment, caused to mature into nerve cells once delivered to a target site. The invention contemplates medicament compositions that include stem cells (neuro or otherwise), including homographs and allographs, adhesive peptides, substances which inhibit fiberblast growth, genetically modified cells which produce useful exogenous substances, nerve growth factor (NGF), and previously harvested cells from a living body. In another aspect, the invention contemplates the replication of cells in a reservoir, for example, to keep cells alive in a dormant state until infusion.

Still another aspect of the invention provides a particular treatment system for Parkinsonian patients in which stem cells are introduced into the living body and provided with other factors that encourage the cells to develop into dopamine-producing cells. Such cells are introduced into the existing cell structure, which is used as a framework for cell growth.

Yet another aspect of the invention provides a particular treatment system for patients who have experienced trauma to the CNS, where a carefully designed medicament composition is delivered to a gap in the nerve structure and newly introduced living cells fill the gap in an organized fashion providing a bridge for nerve impulses traversing the gap, restoring peripheral neural control of distal structures.

The unique advantages provided by the invention have application to the rebuilding or regeneration of tissue structures including nerves, bone, cartilage, tendons and organs. The prolonged infusion of a carefully designed composition operates to foster the development of tissue in cases, for example, where a living body has inadequate resources to provide for regeneration on its own. The invention is also advantageous in providing a comprehensive medicament composition including living cells and the substances required to sustain the life of those cells, to provide a microenvironment that produces therapeutic agents, such as dopamine in applications for treating Parkinsonian patients.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 3 is a block diagram depicting an exemplary method of treating Parkinsonian patients according to the invention; and FIG. 4 is a block diagram depicting an exemplary method of treating a traumatized target area of the CNS according to the invention.

DETAILED DESCRIPTION OF THE INVENTION

As explained in more detail below, the present invention overcomes the above-noted and other shortcomings of known systems by providing an infusion system for delivering a carefully tailored medicament composition to create and maintain a comprehensive microenvironment in a target area of a living body for therapeutic effect.

Figure 1:
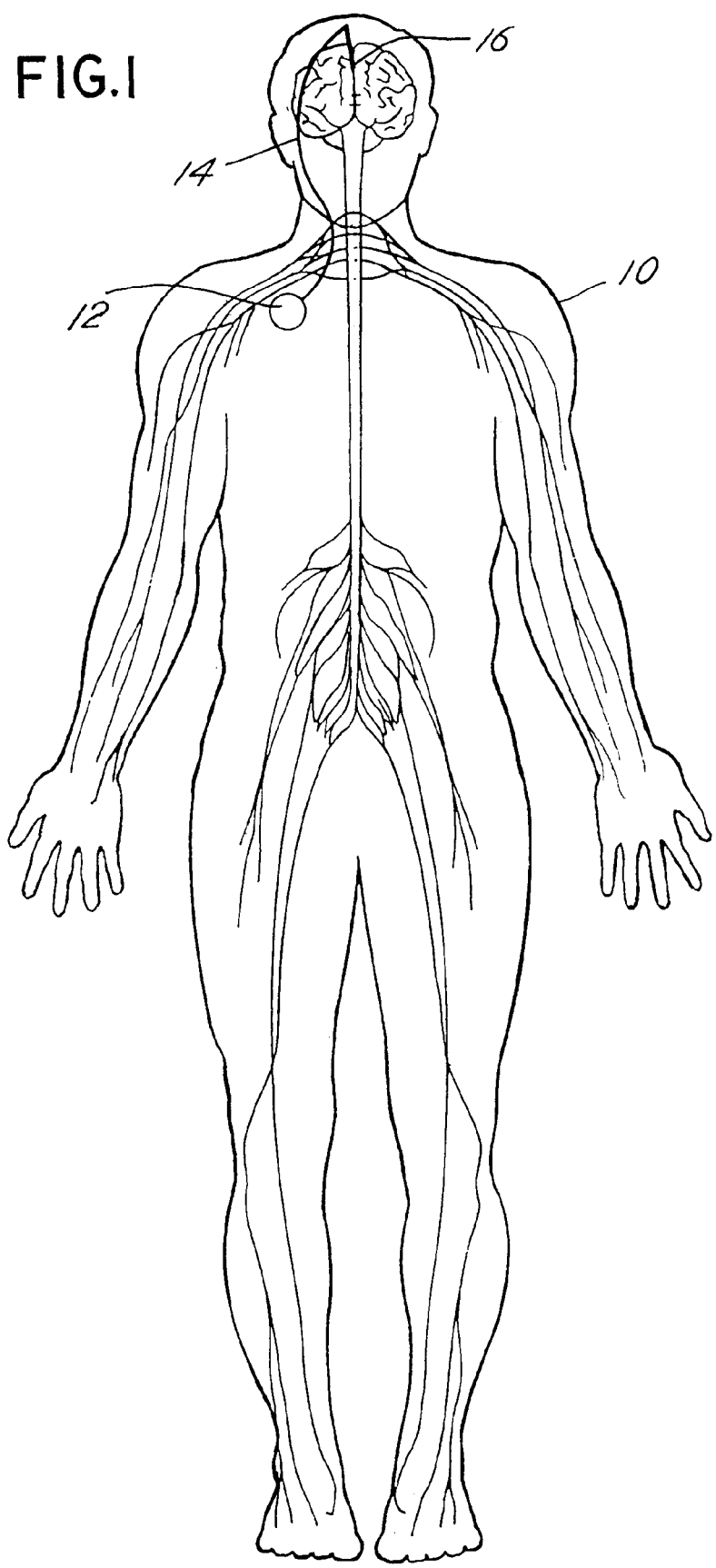
FIG. 1 is a plan view of an exemplary system according to the invention, shown implanted in a living body.

FIG. 1 illustrates an exemplary apparatus for accomplishing the invention. A living body 10 is provided with an implanted infusion device 12, including at least one catheter 14 for conveying a medicament composition from the infusion device 12 to a target area 16. The general details of infusion device 12, which is preferably an infusion pump, modified to accommodate a desired medicament composition, are similar to the SYNCHROMED pump developed by Medtronic. Such modifications may include the elimination of "dead-end" volumes which might provide potential areas for cell aggregation. Moreover, the surfaces within the pump which are encountered by the medicament composition could be coated with materials that encourage cell preservation and inhibit cell aggregation. In accordance with the invention, infusion device 12 is provided with one or more reservoirs for containing respective medicament compositions necessary for maintaining the desired microenvironment at target area 16. One reservoir may contain living cells while another would contain other factors which foster stem cell growth into a particular desired mature cell type. The pump could incorporate features such as those described in U.S. Pat. No. 5,769,823, the entire writing of which is incorporated herein by reference. The invention also contemplates the use of plural implantable pumps, with one pump configured to deliver living cells and the other pump configured to deliver factors which foster growth of those living cells into a particular desired mature cell type.

As used herein, the term "medicament composition" refers to any substance or mixture of substances, both living and non-living, which provide a therapeutic effect to the target area. Medicament compositions contemplated by the invention include stem cells (neural progenitors, both homographic and allographic), neurotrophic factors, including proteins, nerve growth factors, genetically modified cells, including those which produce enzymes, co-factors, neurotransmitters and trophins, adhesive peptides and previously harvested cells from a patient.

The substances that constitute medicament compositions of the invention fall within several categories of agents, including growth factor agents, extracellular matrixes, and cell components. Growth factor agents enhance or encourage the growth of tissues and may include embryonic tissue cells, fluid from embryonic tissue cells, tissues and genetically engineered agents, such as Nerve Growth Factor (NGF), which has been produced through genetic cloning. Extracellular matrixes include those agents which form surrounding materials, support structures or connective tissues, such as collagen, laminin, and fibronectin, which are basement membrane components of the extracellular matrix or which provide directional clues guiding the growth or regeneration of the tissues, such as target derived neuronotrophic factors. Cell components include those agents which form components of the regenerating tissues or tissue structures associated with the regenerating tissues. Cell components used in the regeneration of nerve tissues, for example, may include Schwann cells, which comprise support cells for nerve tissues, glial cells, and fibroblasts.

In the case of nerve regeneration, therefore, the possible agents include neurite promoting factors, surface active agents, neurotrophic agents, humoral agents, and chemical agents causing or enhancing the regeneration process. Examples of such would include collagen, laminin, fibronectin, living cells including Schwann cells, glial cells, dorsal root ganglia cells, neural crest cells and neural and supportive agents. Still further examples of possible agents would include, but not be limited to, nerve growth factor (NGF), ciliary neuronotrophic factor (CNTF), motor nerve growth factor (MNGF), neural cell adhesion molecules (N-CAM), N-Cadherin, fibrin, hormones such as estrogen, testosterone, thyroid hormone, corticotropin, and insulin, catalase, acidic fibroblast growth factor (aFGF), basic fibroblast growth factor (bFGF), forskolin, glia-derived protease inhibitor (GdNPF), ganglioside GM-1, insulin-like growth factor, isaxonine, leupeptin, muscle basal lamina pyronin, and Hyaluronic Acid.

Those of ordinary skill in the art will recognize that the above listed medicament compositions are only exemplary and representative and are not intended to be a limiting definition of the possible medicament compositions that may be used in the regeneration process and that yet further medicament compositions may be defined for each form of tissue to be regenerated.

Figure 2:
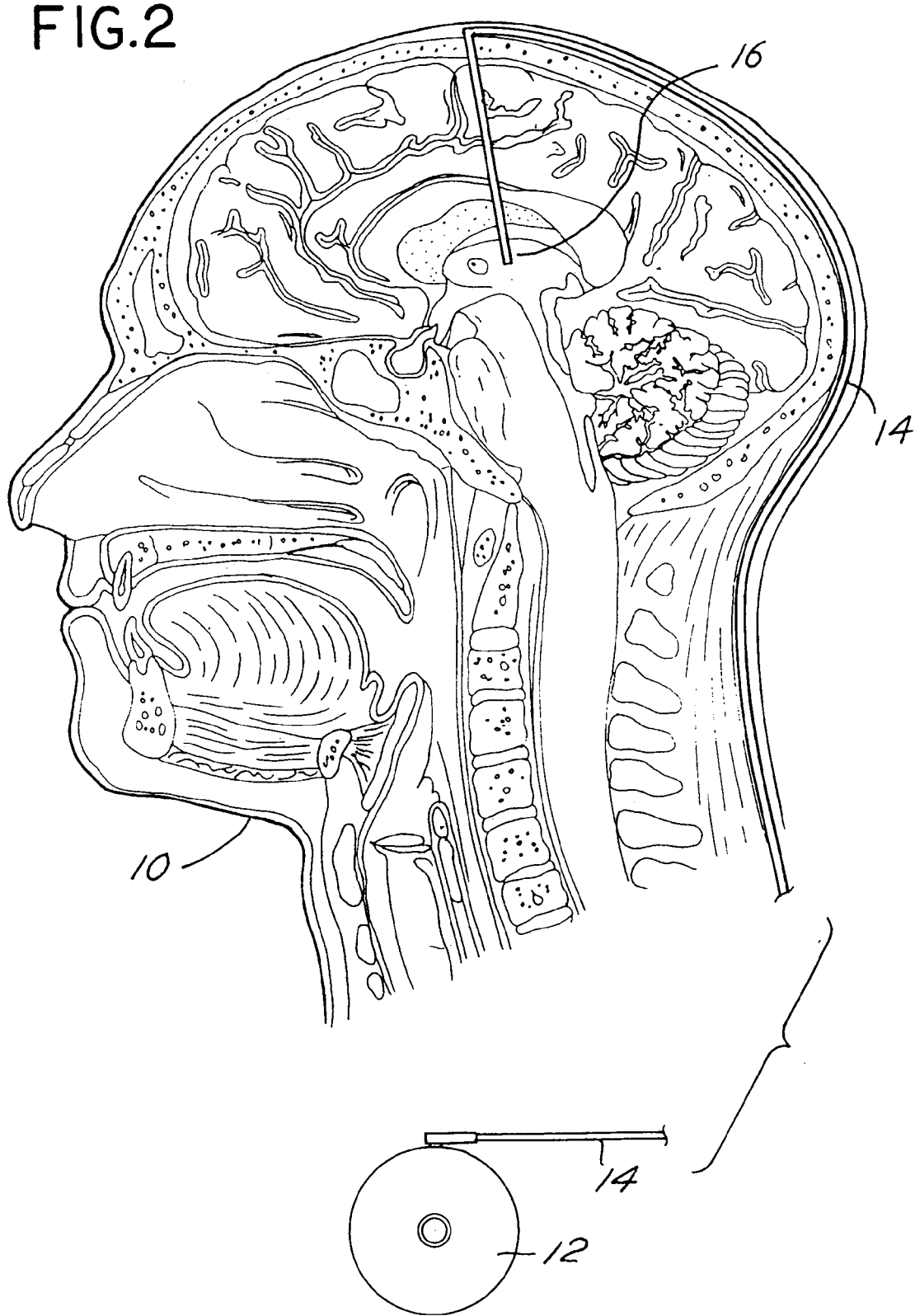
FIG. 2 illustrates an exemplary system according to the invention, for infusing a medicament composition to a target area in a human brain.

Referring to FIG. 2, in an exemplary application of the invention for treating Parkinsonian patients, a medicament composition of stem cells is delivered to the basal ganglia area of the human brain and, once they reach the target area of the basal ganglia, develop into dopamine-producing cells owing to the introduction of appropriate factors. The distal end of catheter 14 may be implanted in a portion of the basal ganglia of the human brain using known implantation techniques. The medicament composition stored in the reservoir of infusion pump 12 is delivered via catheter 14, at a controlled rate, to the target site 16 in the human brain.

Referring additionally to FIG. 3, in accordance with another aspect of the invention, the infusion device 12 delivers a medicament composition that includes living cells, which develop into cells that naturally produce dopamine once in the target area. In addition, the medicament composition is provided with substances which support cell life, such as cell nutrients or substances which influence or foster particular cell effluents. The native cell framework or existing cell structure 18, within the target area 16, provides for the mechanical support of the infused cells. In accordance with the invention, a constant, prolonged microenvironment is provided through the living cells infused to the target area, as well as the additional cell-supporting substances provided in the medicament composition.

An exemplary system for treating a traumatized area of the CNS is illustrated in block diagram form in FIG. 4. Here, the microenvironment is designed to encourage the bridging of nerve structures using new cells, connecting the distal and proximal sections of damaged nerves. Reconnection may be fostered using known techniques for axonal regeneration and synaptogenesis. Stem cells are conveyed via the infusion device 12 to a gap 22 in the nerve cell structure in target area 16.

Those of ordinary skill in the art will recognize that the infusion device 12 may require certain modifications depending on the medicament composition for which it is configured. For example, if living cells are incorporated into the medicament composition, the internal components of the infusion device 12 would require modification so as not to jeopardize the integrity of the living cells contained therein. Such modifications may include the elimination of sharp or narrow passages within the infusion device to avoid damage to cellular structures. The invention contemplates providing for cell replication in a reservoir, for example, to maintain living cells in a dormant state until infusion. For example, vitamin A derivative retinoic acid can stimulate stem cells to produce neurons, perhaps by interacting with stem cell receptors to foster the development of nerve tissue.

Those skilled in the art will recognize that the preferred embodiments described above may be altered or modified without departing from the true spirit and scope of the invention, as defined in the accompanying claims.

What is claimed is:

1. A method of maintaining a microenvironment in a living body comprising the steps of:
    implanting an infusion device in the living body, the infusion device having a reservoir containing a first medicament composition;
    delivering the medicament composition, via the infusion device, to a target area of the living body to maintain a microenvironment in the target area; and
    implanting an additional infusion device to deliver a second medicament composition to foster the growth of cells in the first medicament composition.

2. The method of claim 1, further comprising the step of introducing living cells to the target area.

3. The method of claim 2, further comprising the step of providing additional substances in the first medicament composition to support the living cells.

\* \* \* \* \*